United States Patent [19]

Frank et al.

[11] 4,349,351

[45] Sep. 14, 1982

[54] REAGENT FOR THE DETERMINATION OF HAEMOGLOBIN

[75] Inventors: Georg Frank; Klaus Wehling, both of Wuppertal, Fed. Rep. of Germany

[73] Assignee: Bayer Aktiengesellschaft, Leverkusen, Fed. Rep. of Germany

[21] Appl. No.: 271,073

[22] Filed: Jun. 8, 1981

[30] Foreign Application Priority Data

Jul. 1, 1980 [DE] Fed. Rep. of Germany ....... 3024835

[51] Int. Cl.³ ............................................. G01N 33/72
[52] U.S. Cl. ..................................... 23/230 B; 23/913; 252/408; 422/61
[58] Field of Search .............. 23/230 B, 913; 252/408; 422/61, 102

[56] References Cited

U.S. PATENT DOCUMENTS

| | | | |
|---|---|---|---|
| 3,546,131 | 12/1970 | Stern et al. | 23/230 B |
| 3,607,695 | 9/1971 | Schneider | 23/230 B |
| 3,663,175 | 5/1972 | Depositar et al. | 23/230 B |
| 3,964,865 | 6/1976 | Das | 23/230 B |
| 3,992,150 | 11/1976 | Retzer | 23/230 B X |

Primary Examiner—Arnold Turk
Attorney, Agent, or Firm—Sprung, Horn, Kramer & Woods

[57] ABSTRACT

A reagent for the determination of haemoglobin comprising an aqueous solution of potassium cyanide, potassium hexacyanoferrate-III, a buffer substance and a detergent, wherein the pH value is in the range of 7.1 to 7.3 and the potassium cyanide concentration is in the 90 to 120 mg/liter range. The reagent can be used with plastic throw-away cells, particularly polystyrene cells.

4 Claims, No Drawings

REAGENT FOR THE DETERMINATION OF HAEMOGLOBIN

The invention relates to a reagent for the determination of haemoglobin, for use in plastic throwaway cells, which consists of a certain aqueous solution of potassium cyanide, potassium hexacyanoferrate-III, a buffer substance for adjustment of the pH value and a detergent. This reagent is based on the internationally recognised ICSH reference method, (see International Committee for Standardization in Haematology: Recommendations for Haemoglobinometry in Human Blood, British Journal of Haematology 13 (1967) Suppl. 71–75).

The haemiglobin cyanide method is at present regarded as the most accurate process for the determination of haemoglobin (see W. G. Zijlstra and E. J. van Kampen: Standardization of Haemoglobinometry, I. The Extinction Coefficient of Haemiglobin Cyanide, Clinica Chimica Acta 5 (1960) 719–726; E. J. van Kampen and W. G. Zijlstra: Standardisation of Haemoglobinometry, II. The Haemiglobin Cyanide Method, Clinica Chimica Acta 6 (1961) 538–544; and Bestimmung des Hämoglobingehaltes im Blut (Determination of the Haemoglobin Content of Blood), Draft Standard Specification DIN 58,931, sheet 1, November 1970.

In addition to the customary test packs, ready-to-use test kits which enable the user to carry out the determination rapidly and in a simple manner without having to make up the reagent himself are also available for the determination of haemoglobin. In these "ready-to-use test kits", which are also called mono-tests, single-tests or single-glass tests, small glass bottles are filled with the haemoglobin reagent and this reagent must still be transferred into cells for the measurement.

In some cases, the reagent is also available in round cells in which the haemoglobin determination can be carried out directly. These round cells are also made of glass.

Cells which can be sealed have recently been disclosed (see DT-OS (German Published Specification) No. 2,422,260); these are in the form of plastics throwaway measuring cells (preferably made of polystyrene) and are sealed air-tight with a plastics lid.

In the case of mass production, the lid is attached to the cell by welding, for example ultrasonically. The lid has a prescribed breaking point, which can be broken open by means of a peg. The sample to be analysed can be introduced into the cell through the opening thus produced in the cell lid.

The cells described in the abovementioned Offenlegungsschrift fulfil, to a large extent, the requirements of a "ready-to-use test kit". It is not necessary for the user either to dissolve reagents or mix different solutions exactly or transfer the finished reagent/sample mixture into a measuring vessel. He has only to introduce the sample to be analysed into the cell by exact metering, which can be effected, for example, simply by means of volume-calibrated glass capillaries, and to transfer the cell to the measuring unit (a photometer).

Possible sources of error (e.g. in pipetting) are thereby excluded from the beginning, and the analysis operation is simplified to such an extent that even unskilled personnel can carry out the analysis correctly.

However, using throw-away measuring cells has its problems. Glass is excluded as a material for throw-away measuring cells since glass cells of the quality required for photometric measurements are much too expensive. The use of plastics, for example polystyrene, indeed permits low-cost mass production of throwaway measuring cells, but frequently presents problems with respect to the life of the reagents.

Thus, polystyrene is permeable to many gases. This has an adverse effect, for example, on the life of the reagent for the determination of haemoglobin as haemiglobin cyanide. As mentioned above, in addition to a buffer substance and a detergent for haemolysis of the erythrocytes, this reagent also contains, potassium hexacyanoferrate-III, which oxidises haemoglobin to haemiglobin, and KCN, which converts haemiglobin into haemiglobin cyanide. The haemiglobin cyanide is then determined photometrically.

The KCN contained in the reagent is in equilibrium with HCN in the gas space above the liquid. However, HCN can diffuse through the polystyrene wall of the cell, so that the CN content of the reagent decreases with a half-life of about 4 weeks. This results in a life of a reagent which is insufficient for the reagent to be sold.

DE-AS (German Published Specification) No. 2,721,942 describes a process which overcomes these problems of the life.

In the process described, one reactant—KCN in the case of the determination of haemoglobin—is applied in the form of a solid to the inner surface of the glass capillary used for metering the sample.

Long lives (18–24 months) are achieved by transferring the unstable component—the KCN—from the reaction solution into the capillary for metering the sample.

The disadvantage of the process described is the fact that the capillaries coated with KCN on the inner surface must be manufactured with great accuracy, and the manufacture is correspondingly expensive.

The object of the present invention is thus to provide a less expensive process in order to ensure the competitiveness of the haemoglobin ready-to-use cell, which the intended solution having an equivalent quality This applies, in particular, with respect to the precision and accuracy of the haemoglobin determination and also respect to the reaction time required.

Various experiments have already been carried out to produce a haemoglobin reagent which is stable in plastics ready-to-use cells.

Thus, for example, the pH value of the reagent has been shifted to the alkaline range in order to stabilise the cyanide in the reagent. Better lives are also thereby achieved. A decisive disadvantage of the process is, however, that the reaction time is considerably longer. Thus, the conversion of haemoglobin into haemiglobin cyanide with a reagent such as described, for example, in the abovementioned draft standard specification DIN 58,931, sheet 1, of November 1970, has ended after a reaction time of 3 minutes. If the pH value of the reagent is now shifted from pH 7.2 to pH 8.2 without changing other constituents, this reaction time is extended to 12 to 15 minutes. This is a considerable disadvantage, for example for emergency determinations.

Other manufacturers have attempted to obtain a reagent which is stable in plastic cells by increasing the phosphate buffer concentration from 2.5 mmoles to 10 mmoles. However, these attempts have also been unsuccessful.

A further disadvantage of increasing the phosphate buffer concentration is the fact that this has an adverse effect on the stability of the $K_3[Fe(CN)_6]$ complex.

Attempts to achieve a sufficient life of the haemoglobin reagent in plastic cells by metering in an excess of KCN fail for two reasons. On the one hand, the half-life, of about 4 weeks, of the KCN in plastic ready-to-use cells is very short, so that 32 times the nominal concentration (which would be about 2,080 mg for a nominal concentration of 65.12 mg of KCN per liter of reagent) would have to be employed for a life of one year. On the other hand, the life of the $K_3[Fe(CN)_6]$ complex is impaired by high KCN concentrations. For example, whilst the concentration of the $K_3[Fe(CN)_6]$ remains constant at about 200 mg per liter for 1 year in the case of an initial concentration of 65 mg of KCN per liter of reagent, in the case of an initial KCN concentration of 860 mg per liter it falls from 200 mg per liter to 130 mg per liter in the course of 18 weeks, and is thus in a range in which significant deviations from the nominal value occur in the determination of haemoglobin.

Various attempts have also been made to achieve a better life of the haemoglobin reagent by adding preservatives or stabilisers. Substances such as benzyl alcohol, p-chloro-m-cresol, solbrol, polyethylene glycol and collidone have been used for this. However, these attempts have also met with no success.

Surprisingly, a reagent which is based on the ICSH reference method and is suitable for use in plastic throw-away cells and which has the required long-term stability has now been found.

According to the present invention there is provided a reagent for the determination of haemoglobin for use in plastics throw-away cells, which consists essentially of an aqueous solution of potassium cyanide, potassium hexacyanoferrate-III, a buffer substance for adjustment of the pH value and a detergent, in which the pH value is adjusted within a narrow range of 7.1 to 7.3, with the aid of the buffer substance, and the potassium cyanide concentration is 90 to 120 mg/liter (1.38 to 1.85 mmoles/liter).

When this reagent is used in polystyrene ready-to-use cells, a quasi-stable state develops after a short time, so that a life of at least 12 months is achieved in polystyrene ready-to-use cells. The present invention thus also comprises plastics, especially polystyrene, throw-away cells comprising a solution of the present invention.

In the stable state, the reagent corresponds to that of the ICSH reference method. There are no differences between the two reagents with respect to the rate of conversion of haemoglobin into haemiglobin cyanide (rate of reaction). The results of 431 haemoglobin determinations in which the haemoglobin content of in each case one blood sample was determined both using the ISCH reference method and using the reagent according to the invention show a very good agreement. An average haemoglobin value of 15.0 g/100 ml was found with the ICSH reference method. An average value of 14.8 g/100 ml was obtained with the reagent according to the invention.

The pairs of values found were correlated. A correlation line was calculated as follows:

$$x = 1.0139 \cdot y - 0.0333,$$

in which
 x corresponds to the values determined using the ICSH reference method and
 y corresponds to the values determined with the reagent according to the invention.

The correlation coefficient was calculated as $r = 0.9934$.

The following Example illustrates the preparation of a reagent according to the present invention.

EXAMPLE

A haemoglobin reagent of the following composition was prepared, for filling a polystyrene throw-away measuring cell: 1.54 mmoles/liter of potassium cyanide, 0.6 mmole/liter of potassium hexacyanoferrate-III, 2.5 mmoles/liter of potassium phosphate buffer of pH 7.1 to 7.3 and 0.05% of detergent (for example saponin).

1.25 ml of solution were obtained therefrom, using distilled water as the solvent. If appropriate, small amounts of NaCl (about 1.5 mmoles/liter) could also be added to this solution, in order to avoid cloudiness.

What is claimed is:

1. In a reagent for the determination of haemoglobin consisting essentially of a solution in distilled or deionized water of potassium cyanide, potassium hexacyanoferrate-III, a buffer substance and a detergent, the improvement wherein the pH value is in the range of from 7.1 to 7.3 and the potassium cyanide concentration is in the range of from 90 to 120 mg/liter.

2. An inert plastic throw-away cell for the determination of haemoglobin containing a reagent of claim 1.

3. An inert plastic throw-away cell of claim 2 in which the said cell is formed from polystyrene.

4. A method for the determination of haemoglobin which comprises adding whole blood to an inert plastic throw-away cell for the determination of haemoglobin containing a reagent of claim 1 and measuring the haemoglobin therefrom.

* * * * *